US006233473B1

(12) United States Patent
Shepherd et al.

(10) Patent No.: US 6,233,473 B1
(45) Date of Patent: May 15, 2001

(54) DETERMINING BODY COMPOSITION USING FAN BEAM DUAL-ENERGY X-RAY ABSORPTIOMETRY

(75) Inventors: John A. Shepherd, Novato, CA (US); Thomas L. Kelly, Groveland, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 09/292,480

(22) Filed: Apr. 15, 1999

Related U.S. Application Data

(60) Provisional application No. 60/120,289, filed on Feb. 16, 1999.

(51) Int. Cl.[7] .......................................................... A61B 5/05
(52) U.S. Cl. ............................................. 600/407; 378/54
(58) Field of Search .................................... 600/407, 408; 378/4, 21, 37, 53, 54, 98.9; 374/45; 514/556

(56) References Cited

U.S. PATENT DOCUMENTS 6,090,849 * 7/2000 Teeter et al. ........................... 514/556
6,123,451 * 9/2000 Schaefer et al. ........................ 374/45

* cited by examiner

Primary Examiner—George Manuel
(74) Attorney, Agent, or Firm—Cooper & Dunham LLP

(57) ABSTRACT

True body composition is estimated using a dual-energy, fan-shaped distribution of x-rays and signal processing that corrects for mass magnification and other effects due to the geometry of the measurement system. To avoid inaccuracies due to beam hardening and certain other effects, the thickness of attenuating material along respective raypaths is obtained through using a four-dimensional look-up table derived experimentally from step-wedge measurements. To correct for mass magnification effects due to using a fan-shaped distribution of x-rays, another look-up table and interpolation between table entries are used to convert projected mass to true mass.

5 Claims, 3 Drawing Sheets

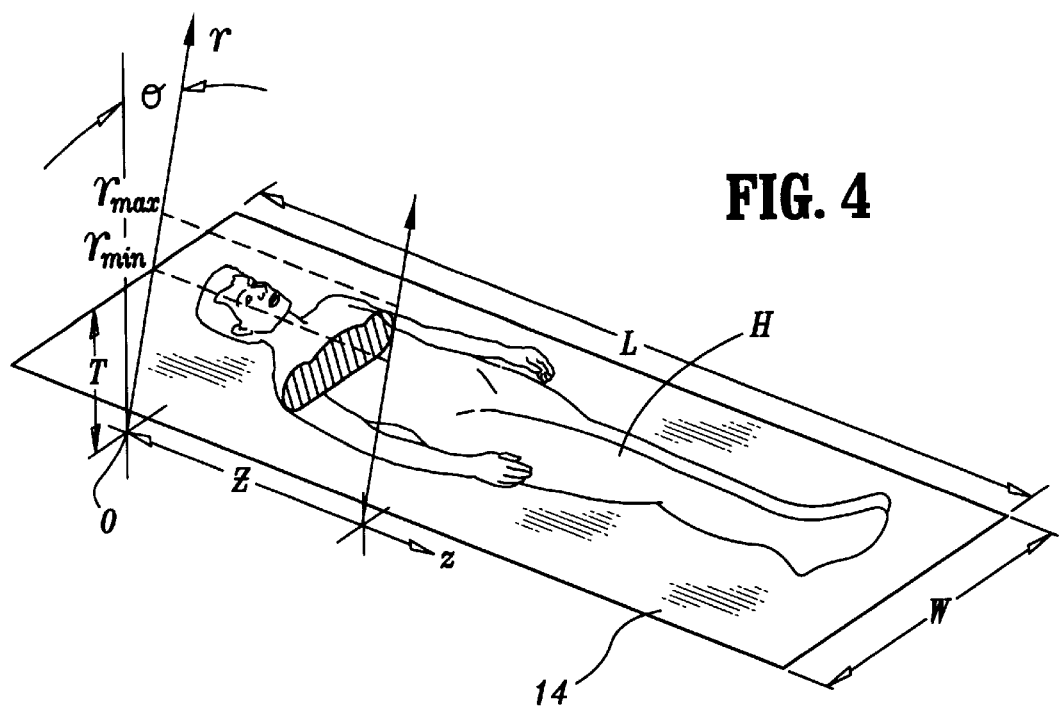
FIG. 4
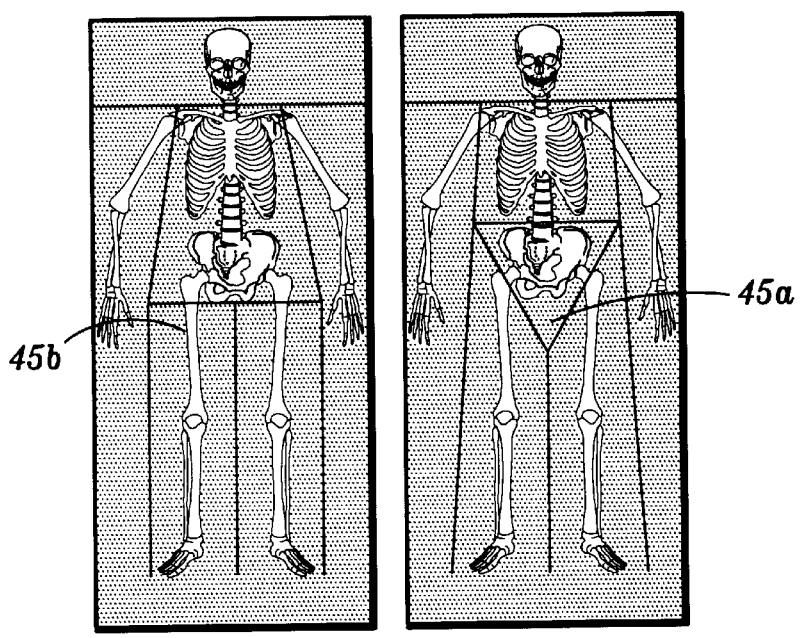
FIG. 6B  FIG. 6A

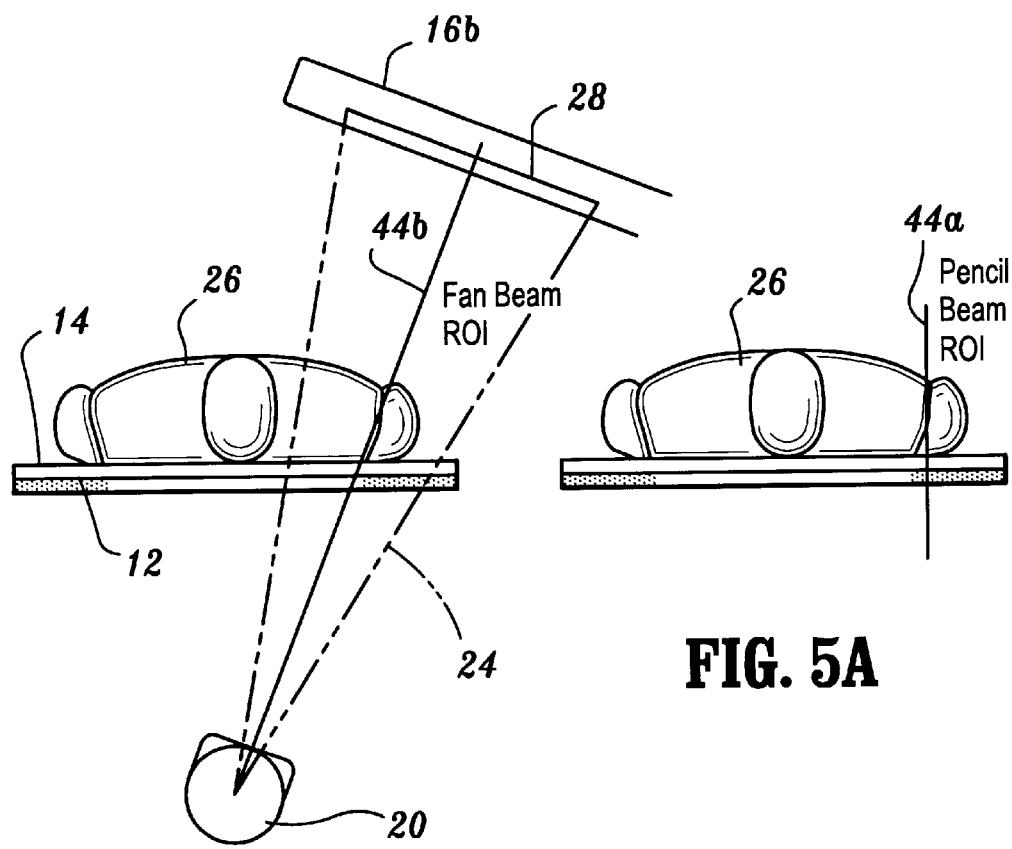
FIG. 5A
FIG. 5B
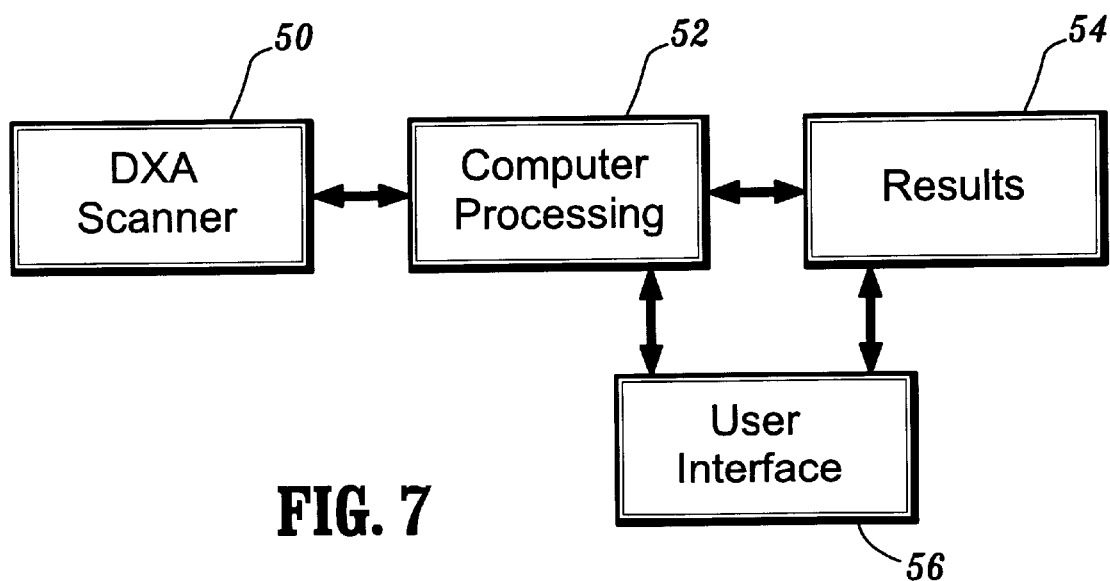
FIG. 7

DETERMINING BODY COMPOSITION USING FAN BEAM DUAL-ENERGY X-RAY ABSORPTIOMETRY

REFERENCE TO RELATED APPLICATION

This present application claims the benefit of provisional application Ser. No. 60/120,289, filed on Feb. 16, 1999, which is hereby incorporated herein by reference.

FIELD

This patent specification pertains to the field of using x-rays to determine internal characteristics of patients or objects, and more specifically to using dual-energy x-ray absorptiometry to determine whole body and regional composition. Still more specifically, this specification is in the field of using a fan-shaped distribution of x-rays for such purposes.

BACKGROUND

The determination of body composition (e.g., fat mass, lean mass, etc.) of a living human subject has been recognized as having medical utility for diverse predictive, diagnostic, and monitoring purposes. Body composition can also be of interest where x-rays irradiate non-human subjects or inanimate objects. For some purposes, whole body composition is measured or estimated while for other purposes the composition of parts of the body are of interest, such as limbs, hips, etc.

Systems using dual-energy x-ray absorptiometry (DXA) have long been used to measure or estimate parameters such as bone mineral density (BMD), e.g., systems commercially available from the assignee hereof under trade designations such as the QDR 4500 and QDR 2000 product lines. Other types of systems have been used for BMD measurement to a lesser extent, such as quantitative computer-aided tomography (QCT) and single photon absorptiometry (SPA) using isotopes as radiation sources. DXA systems also have been used to measure or estimate body composition, both for the whole body and for regions thereof. See, e.g.: Kelly T L, Berger N and Richardson T L, *Appl. Radiat. Isot., Vol.* 49, No. 5/6, pp. 511–513, 1988; Fuerst T and Genant H K (1996) Evaluation of body composition and total bone mass with the Hologic QDR 4500, *Osteoporisis International* 6, s202; Prince R, Price R. Gutteridge D, Retallack R, Dick I, Lemmon J, Hall S, LeDain S 1995 Comparison of bone mineral density measurement between the Hologic QDR2000 and QDR4500A, *J Bone Miner Res* 10 (Suppl 1): s272; Kelly T (1996) Whole Body Enhancements: Free software upgrades available for QDR-4500A and QDR-4500W users with and without body composition option QDR Insights, *New Developments in Bone Mineral Measurements*, Vol. 7, p. 15. Some DXA systems use a single, pencil beam shaped beam of radiation that scans the body, typically in a rectilinear fashion, and take dual-energy measurement at each of the many pixel positions arranged in a rectangular pixel matrix. Others, such as the QDR-4500A systems use a wider, fan-shaped distribution of x-rays, and can scan the entire body, typically in three scans along the length of the body, combined to simulate the effect of scanning with a single fan-shaped distribution that is sufficiently wide to encompass the entire body width, as described in commonly assigned U.S. Pat. No. 5,748,705. The patent and publications cited above are hereby incorporated by reference in this patent specification as though fully set forth herein.

When pencil-beam systems are used for body composition measurements, the attenuation measurement for all the pixels are obtained by measuring the intensity of x-rays that travel along essentially parallel paths. However, when a system with a fan-shaped x-ray distribution is used, there are geometric and other factors that can complicate body fat computations and introduce inaccuracies. In an effort to account for such factors, Hologic released a body composition option for its 4500A system. The option has been used commercially in this country since its introduction in 1996, but it is believed that a need still remains to improve body composition analysis in systems using fan-shaped distributions of x-rays.

SUMMARY

This patent specification describes a new approach to body composition analysis in DXA systems using a fan-shaped distribution of x-rays that accounts not only for the factors previously considered in the 1996 option for the QDR 4500A systems, but also for mass magnification effects that the system geometry entails. The new approach makes use of the realization that accuracy can be improved significantly by taking into account the apparent changes in measured mass with changes of the location of the mass along the raypaths from the x-ray source to the x-ray detector, and by finding an effective way to make corrections for such changes in apparent mass.

When a fan-shaped distribution of x-rays is used, e.g., with a DXA system that includes a patient table on which a supine patient reclines, a magnification effect takes place that causes a mass element nearer the table surface to be weighted more heavily (to appear to have more mass) than an identical mass element further away from the table surface. Thus, one unit of mass can be measured correctly as one unit if on the table surface but as less than a unit of mass if at some height above the table surface. For a supine patient on the table surface, a mass element at the patient's back can appear to have more mass than an identical mass element at the patient's abdomen. While in known earlier work the measured mass was calibrated to be nominally correct for the average-size subject, the mass for thin subjects could be overestimated and the mass for obese subjects could be underestimated.

The detailed disclosure set forth herein describes the recognition of the cause for this inaccuracy and a solution that makes the body composition more accurate.

BRIEF DESCRIPTION OF THE DRAWINGS

FIG. 4 is a diagrammatic isometric view of a patient on a table of the system of FIG. 1, for reference in defining a coordinate system.

FIGS. 5*a* and 5*b* are simplified and diagrammatic sectional views illustrating a difference between using a pencil-beam (FIG. 5*a*) and a fan-beam system (FIG. 5*b*).

FIGS. 6*a* and 6*b* illustrate two systems for defining regions of interest—a previously used system (FIG. 6*a*) and a system used when applying the body composition analysis described in this patent specification (FIG. 6*b*).

FIG. 7 is a block diagram of a system useful for estimating true body composition using a fan-shaped distribution of x-rays.

DETAILED DESCRIPTION

Figure 1:
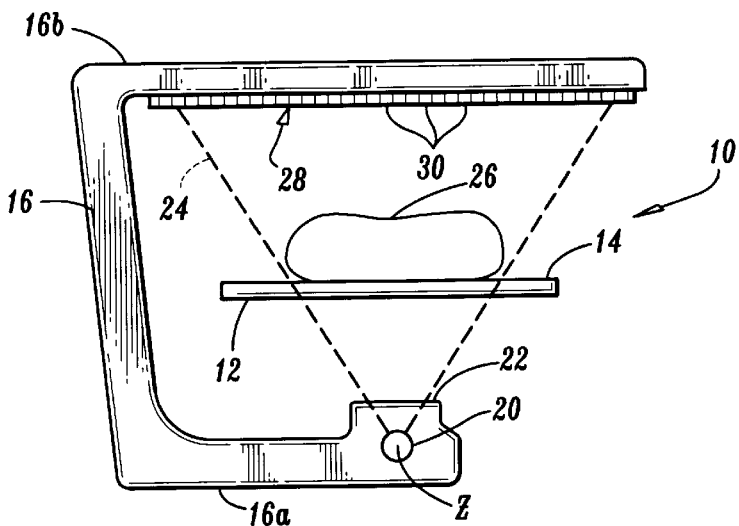
FIG. 1 is a simplified and schematic cross-sectional elevation illustrating a fan-shaped distribution of x-rays in a DXA system in which the body composition analysis described herein can be practiced.
Figure 2:
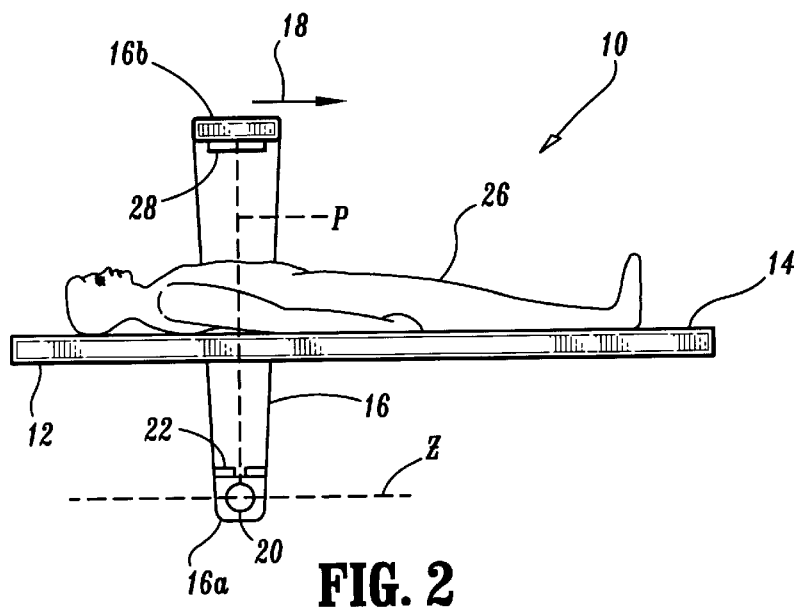
FIG. 2 is a simplified and schematic longitudinal elevation of the DXA system of FIG. 1.
Figure 3:
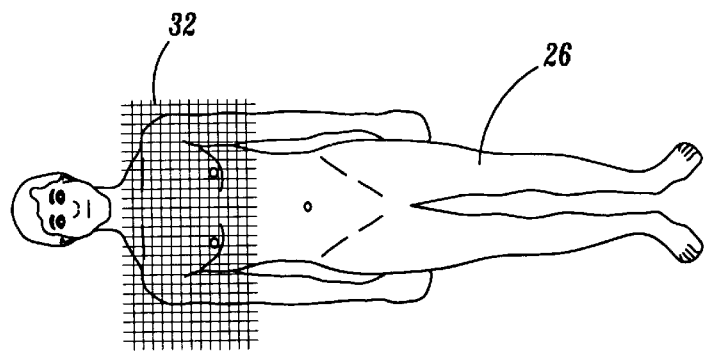
FIG. 3 is simplified representation of a human subject scanned with the system of FIG. 1 to obtain raw data measurements for pixels in a rectangular matrix.

Referring to FIGS. 1–3, a DXA system 10 such as in the QDR 4500A product includes a patient table 12 having a support surface 14 that can be considered horizontal and planar in this simplified explanation. A human subject 26 is supine on surface 14, with the length of the patient being along a horizontal longitudinal axis defined as the z-axis. A C-arm 16 has portions 16a and 16b extending below and above table 10, respectively, and is mounted in suitable structure (not shown) for moving parallel to the z-axis along the length of patient H. Lower portion 16a of the C-arm carries an x-ray source 20 that can emit x-rays shaped by a collimator 22 into a fan-shaped distribution 24 conforming to a plane perpendicular to the z-axis. The x-ray distribution can be continuous within the angle thereof or can be made up, or considered to be made up, of individual narrower beams. The x-ray distribution 24 encompasses the patient and impinges on an x-ray detector 28 that can comprise an array of individual x-ray elements 30 or can be a continuous detector where measurements for different positions along the detector can be defined, or can be another form of detector of x-rays. As C-arm 16 moves along the z-axis, x-ray distribution 24 scans patient 26 and x-ray detector 28 produces a succession of lines of raw x-ray data. Each line corresponds to a particular position of the C-arm in its movement along the z-axis and comprises a number of individual measurements, each for a respective pixel in the line, i.e., represents the attenuation that the x-rays have suffered in traveling from source 20 to a respective pixel position. For example, a pixel measurement is obtained from each respective detector element 30 for each line. A DXA system takes a high energy measurement H and a lower energy measurement L, so that each pixel measurement comprises an high measurement H and a low energy measurement L. This can be done by rapidly alternating the energy level of the x-rays from source 20 between a higher and a lower range, for example by rapidly switching the x-ray tube and/or rotating or otherwise moving a suitable filter in or out of the x-rays before they reach patient 26, or by operating source 20 to produce a relatively wide x-ray energy range but using an x-ray detector 28 that can discriminate between energy ranges to produce H and L measurements for each pixel position in a rectangular array such as illustrated in FIG. 3. The H and L x-ray measurements for the respective pixel positions are computer-processed as known in the art to derive estimates of parameters such as BMD.

While FIGS. 1 and 2 illustrate an x-ray distribution 24 wide enough to encompass the entire patient, and a C-arm 16 that moves only along the z-axis, typically such a wide x-ray distribution is simulated by using a narrower-angle distribution, such as illustrated in FIG. 5b, that scans along the z-axis in several (e.g., three) successive scans. At least one, and typically both, of table 12 and C-arm 16 move in a plane perpendicular to the z-axis between the scans to keep the vertical distance between the origin of the x-rays and table 12 constant and thereby enable the effective combination of the narrower-angle scans to give the H and L measurements that would have been obtained by the single, wide distribution illustrated in FIG. 1.

Given a divergent distribution of x-rays, such as distribution 24, the mass of an attenuator that is entirely within the x-ray distribution can be estimated from x-ray intensity measurements taken with detector 28 if the height of the attenuator above table 12 is known or can be measured. This is so because attenuation, as measured with detector 28, is proportional to true mass density, not to projected mass density. For example, an attenuator of uniform thickness that remains within x-ray distribution 24 at each of two different heights above table 12 will produce the comparable attenuation measured per unit projected area at detector 28 at each height but the total projected area will differ. At a lower height above table 12, the same attenuator produces a wider projected area at detector 28 than at a greater height above table 12. If one multiplies the projected area at detector 28 to get mass, a different mass would be calculated for each different height of the same attenuator above table 12, an undesirable result.

In principle, the mass through which a raypath of x-rays measured for a pixel passes can be estimated as follows. The dual-energy measurements taken by detector 28 are processed into attenuation measurements and are used to estimate the average density of the column of material (e.g., body tissue) through which the respective raypath passes, using calculations known in the art. The x-ray measurement for the high energy (e.g. 140 kVp) can be used as a measure of tissue thickness along the raypath, i.e., for a given pixel position. The mass of an object traversed by the measured x-rays can be defined as:

$$\text{mass} = \int \rho \, dV$$

where $\rho$ is density in g/cm$^2$ and dV (in cm$^3$) is a volume differential. This relationship can be expressed by the triple integral in the cylindrical coordinates defined in FIG. 4:

$$\text{mass} = \int \int \int \rho(r, \theta, z) \, r \, dr \, d\theta \, dz$$

where the first and third integrals are from 0 to $\infty$ and the second integral is from $-90$ to $+\pi$. To solve the radial integral, the limits of r can be defined as where the density of the body of interest goes to zero at a given angle within the x-ray distribution. For a body 26 on table 12, $r_{min}$ is the distance from the origin of the x-rays within distribution 24 to the top of table 12. That is:

$$r_{min} = T \sec\theta$$

where T is the distance from the origin of the x-rays to the top of table 12 at the center of the x-ray distribution 24. The maximum value of r can be correspondingly defined as:

$$r_{max} = T \sec\theta + t(\theta, z)$$

where $t(\theta, z)$ is the thickness of body 26 along the length of r at angle $\theta$ within x-ray distribution 24.

The measurement for any one pixel is along a raypath, i.e., for a column of material without the ability to directly measure the distribution of attenuation within that column. Accordingly, the average density $\rho(r, \theta, z)$ that is within a raypath to a pixel position and extends in a radial direction r (see coordinate system defined in FIG. 4) can be defined as $\rho(\theta, z)$. To ensure that the entire patient 26 is taken into account, the angle $\theta$ is integrated over the entire patient width, from $-\text{atan}(W/2)$ to $+\text{atan}(W/2)$, where W is the width of table 12, and z is integrated over the length L of table 12. The limits of the triple integral set forth above then become:

0 to L for the first integral;
$-\text{atan}(W/2)$ to $+\text{atan}(W/2)$ for the second integral; and
$T\sec\theta$ to $[T\sec\theta + t(\theta, z)]$ for the third integral. The radial integral can be explicitly solved, and becomes:

$$\text{mass} = \int \int \rho(\theta, z) \, t(\theta, z) \{[t(\theta, z)]/2 + T\sec\theta\} d\theta \, dz,$$

where the limits of the first integral are (0 to L) and the limits of the second integral are $[-\text{atan}(W/2)$ to $+\text{atan}(W/2)]$. This is a general solution for the mass of a patient, or an object, on a flat surface such as table 12, at a distance T from the origin of the x-rays and the coordinate system, with a thickness t (θ, z) along the respective radial direction for each x-ray attenuation measurement for a respective pixel position. The thickness t (θ, z) can be estimated from the high energy measurements H for the respective pixel positions, and the attenuation or density values ρ(θ, z) can be estimated from the high and low measurements (H, L) for the respective pixel positions.

In the case of the QDR 4500A system, the thickness can be estimated in accordance with:

$$t(\theta, z) = [A(E_H)]/[k(E_H, \rho)]$$

where $A(E_H)$ is the high energy x-ray attenuation (dimensionless) measured for the respective pixel position, and $k(E_H, \rho)$ is the linear attenuation coefficient (in units of (1/length)) of the column of material traversed by the raypath giving rise to the measurement for the respective pixel position. The density ρ can be estimated for the individual pixel positions using the patient's % Fat estimates for the respective pixel positions, where the % Fat is estimated from the ratio of high and low x-ray energy measurements for the respective pixel positions as is known in the art.

For practical reasons, such as the effect of beam hardening and other factors, in a preferred embodiment patient thickness is not determined explicitly, by directly solving the mathematical expressions set forth above. Rather, the thickness values for the respective pixel positions are determined from an experimentally established, 4-dimensional look-up table containing high and low x-ray attenuation measured values, density, and patient thickness. The experimental values in this look-up table are found using a calibration step phantom for % Fat and known human density values that correspond to the % Fat values. The entire integral is solved by converting it to a summation with an angular step for the width of a pixel position. The experimental values for the QDR 4500A DXA system are incorporated in the body composition option for that system made commercially available in this country in 1996, and are hereby incorporated by reference in this patent specification. Corresponding values for other systems can be derived using the corresponding methodology of step phantom measurements.

In a preferred embodiment, particularly suitable for DXA systems such as the QDR 4500A, the body composition estimates that were made without directly accounting for magnification effects can be used in a process that converts them to estimates that do account for this effect. In particular, a correction of projected mass to true mass is carried out in accordance with a preferred embodiment by using another experimentally derived look-up table and linearly interpolating corrected pixel position values based on table entries. One example of this look-up table is:

| 1 | 1.01        |             |   |         |       |
|---|-------------|-------------|---|---------|-------|
| 2 | 7, 163, −54, 54 |         |   |         |       |
| 3 | 1.192       | 1.183       | 0 | 1.192 0 | 1.192 |
| 4 | 2.463       | 2.420       | 0 | 2.463 0 | 2.463 |
| 5 | 3.800       | 3.831       | 0 | 3.800 0 | 3.800 |
| 6 | 5.087       | 5.310       | 0 | 5.087 0 | 5.087 |
| 7 | 6.375       | 6.926       | 0 | 6.375 0 | 6.375 |
| 8 | 7.621       | 8.582       | 0 | 7.621 0 | 7.621 |
| 9 | 8.883       | 10.385      | 0 | 8.883 0 | 8.883 |

The values in the table above are factors applied to projected mass estimated based on the body composition process commercially available in the option for the QDR 4500A system as of 1996. In that system, the whole body angle subtends 60° (+/−30° from the center of the fan-shaped x-ray distribution), where this angle is the result of combining the results of three separate passes along the length of the patient table, each pass using a narrower-angle, fan-shaped distribution of x-rays positioned relative to the table such as to effectively form a combined 60° fan-shaped x-ray distribution. For example, the first pass covers the range −30°/−10°, the middle pass covers the −10°/+10° range, and the third pass covers the +10°/+30° range. It can be expected that different correction factors would be required for the different passes, but in fact the 1996 process referred to above already accounts for angular dependence of the measurements by normalizing the physical size of each element 30 of x-ray detector 28 regardless of pixel position, thus obviating a need for different tables to account for mass position corrections. If desired, rather than normalize the measurements to account for angular dependence, the result can be achieved by using three separate, experimentally derived tables for the three passes with the narrower-angle distribution of x-rays.

Referring to the table above, the first column is line numbers. The first line is the version number, so that later versions, if any, can be applied to x-ray data is desired. Line 2 indicates the number of lines of correction factors (7 in this example) and the location of the three passes that make up a set of scan data for a patient or subject. In this example, 163 is the center pixel position of the middle pass, its sum with the number to the right (163−54=109) is the last pixel position in the first pass, and the sum with the last number to the right (163+54=217) is the first pixel position in the last pass. The pixels in a line are numbered starting at 0.

Each of lines 3–9 contains the correction factors, in the form of a projected mass estimate (grams per pixel position) before correction, and a true mass. The first two numbers (1.192 and 1.183) are the projected and the true mass, respectively. The next two numbers (0 and 1.192) are a linear slope and a projected mass for the first pass with the narrower-angle x-ray distribution, where the slope (0) indicates the linear slope showing how the projected mass (1.192 in this case) varies as a function of pixel position number as one moves from one pixel position to another toward the beginning of the line. While in this example the linear slope is zero, in other examples it need not be zero. The last two numbers are the corresponding numbers for the third pass, with the slope (0) indicating how the projected mass varies as a function of pixel position as one moves toward the end of the line for the third pass. It is assumed in this example that the slope for the middle pass also is 0.

With the table set forth above, the true mass T at any pixel position can be calculated from the table entries using the relationship:

$$T = T1 + (M - M1) * [(T2 - T1)/(M2 - M1)]$$

where T2 and T1 are the true masses corresponding to the projected masses M2 and M1. If an estimated projected mass M for a given pixel position is less than the projected mass in line 3 of the table (1.192), then M1 and T1 are take to be 0. If M is greater than the projected mass in the last line of the table, then the last two lines of the table are used in the calculation of true mass.

In the more general case where the slopes are not 0, linear interpolation is used to calculate the projected mass for each line of data and each pixel position within the line, and the interpolated value of projected mass is used to determine which line of the table applies. Letting M1 and M2 be the interpolated values for the two lines, and letting T1 and T2 be the interpolated values for the true mass using the same linear slope, then the above formula for T gives the corrected mass for the more general case.

From the table above, it is apparent that projected mass values below a certain threshold (approximately 3.8 grams) are mapped to lower true mass values for the respective pixel positions, and that projected mass values higher than the threshold are mapped to progressively higher true mass values for the respective pixel position. Lower projected mass values in the table are indicative of thinner mass elements (i.e., shorter columns of matter through which the raypath for the respective pixel position passes). These thinner mass elements, that are undesirably magnified in known prior approaches, but are effectively de-magnified in accordance with the disclosure herein, using a computer implementation of the table set forth above. Similarly, higher values of projected mass are indicative of thicker mass elements (longer columns of matter through which respective raypaths pass on their way to the x-ray detector elements). These thicker mass elements are de-magnified in known prior approaches, but are re-magnified to represent better estimates of true mass values in accordance with a computer implementation of the table set forth above.

The region of interest subjected to the foregoing body composition analysis can be the entire body of a patient or a defined region thereof. Regional body composition estimates can be obtained by interactively graphically or otherwise defining regions of interest (ROI), for example on an x-ray image of the scanned body. In body composition analysis, typical regions of interest are the limbs and the trunk. As illustrated in FIGS. 5a and 6a for the example of a pencil beam scanner and a region of interest that is the arm of a supine patient on table 12, a dividing line for the arm can be drawn on an image of the patient on the basis of vertical raypaths from the x-ray source to the x-ray detector. However, in the same case for a system using a fan-shaped distribution of x-rays, the geometry differs, as illustrated in FIGS. 5b and 6b. The raypaths of interest in this case are not vertical but oblique. When the region of interest is the trunk, or the pelvis and leg regions, for example, the ROI boundary lines drawn on the screen displaying an image of the body should account for the difference in geometry of the relevant raypaths for pencil beam systems and systems using a divergent x-ray distribution such as the QDR 4500A. For example, a modification as illustrated in FIG. 6a has been found useful. This modification defines the pelvis by the illustrated triangle, the legs as the regions below the triangle and inward of the lines separating the arms, and the trunk as the area above the triangle and inward of the lines separating the arms.

The disclosed process and system have been implemented in a QDR 4500A DXA scanner as generally illustrated in FIG. 7, where scanner 50 scans the body of a patient or an object to produce x-ray measurements, a computer processing unit controls scanner 50 and processes x-ray measurements obtained thereby in accordance with the techniques described above under corresponding programming, a unit 54 displays results such as in the form of images as in FIGS. 5a and 5b and in the form of numeric results and graphs such as BMD estimates obtained from estimates from populations matched by age and/or other characteristics, and units 52 and 54 communicate interactively with a user input unit 56. The actual physical arrangement of system components may differ from the functional illustration in FIG. 7.

The disclosure above is mainly in terms of body composition analysis of human patients, but it should be clear that its approach is applicable in other fields as well, such as in body composition analysis of other subjects, such as live animals and carcasses. Finally, while a currently preferred embodiment has been described in detail above, it should be clear that variation that may be currently known or that are later developed or are later made possible by advances in technology also are within the scope of the appended claims also are contemplated and are within the spirit of the detailed disclosure.

What is claimed is:

1. A method of estimating body composition from x-ray measurements made with a fan-shaped distribution of x-rays comprising the steps of:

scanning a body with a fan-shaped distribution of x-rays and with a detector of x-rays to derive dual-energy x-ray measurements for respective pixel positions conforming to a two dimensional projection of the body;

processing the x-ray measurements to derive estimates of projected body mass for the respective pixel positions;

further processing the estimates of projected body mass to derive estimates of true body mass for the respective pixel positions that account for the positions of attenuating material along raypaths from a source of the x-ray distribution to respective positions at the detector.

2. A method as in claim 1 in which said processing comprises relating x-ray measurements to estimates of projected body mass by utilizing a computer implementation of an experimentally derived first look-up table relating dual-energy x-ray measurements, density and body thickness for the respective pixel positions.

3. A method as in claim 2 in which said further processing comprises relating the estimates of projected body mass to true body mass using a computer implementation of a second experimentally derived look-up table and interpolating between entries in said second look-up table as needed for values intermediate entries in said second look-up table.

4. A method as in claim 3 including the step of defining a region of interest in said body and using said estimates of true body mass for the pixel positions matching the region of interest to derive a total body mass estimate for the region of interest.

5. A method as in claim 4 in which the step of defining a region of interest comprises interactively defining the region from user input showing the region of interest on a displayed image of the body.

* * * * *